(12) United States Patent
Bar et al.

(10) Patent No.: US 10,278,820 B2
(45) Date of Patent: May 7, 2019

(54) PERCUTANEOUS VALVE REPAIR AND REPLACEMENT

(71) Applicant: Valfix Medical Ltd., Megadim (IL)

(72) Inventors: Eli Bar, Megadim (IL); Elad Yaacoby, Kfar Shmuel (IL)

(73) Assignee: Valfix Medical Ltd., Tel Aviv (IL)

( * ) Notice: Subject to any disclaimer, the term of this patent is extended or adjusted under 35 U.S.C. 154(b) by 0 days.

(21) Appl. No.: 16/151,363

(22) Filed: Oct. 4, 2018

(65) Prior Publication Data

US 2019/0029827 A1 Jan. 31, 2019

Related U.S. Application Data

(63) Continuation of application No. PCT/IB2017/052331, filed on Apr. 24, 2017.

(60) Provisional application No. 62/327,176, filed on Apr. 25, 2016, provisional application No. 62/337,347, filed on May 17, 2016, provisional application No. 62/453,556, filed on Feb. 2, 2017.

(51) Int. Cl.
*A61F 2/24* (2006.01)
*A61B 17/00* (2006.01)

(52) U.S. Cl.
CPC ............ *A61F 2/2445* (2013.01); *A61F 2/24* (2013.01); *A61F 2/2427* (2013.01); *A61F 2/2466* (2013.01); *A61B 2017/00243* (2013.01); *A61F 2/2409* (2013.01); *A61F 2/2439* (2013.01); *A61F 2/2454* (2013.01); *A61F 2210/0014* (2013.01); *A61F 2220/0016* (2013.01); *A61F 2250/001* (2013.01)

(58) Field of Classification Search
CPC .......... A61B 2017/00783; A61B 2017/00243; A61B 2017/0409; A61B 2017/0417; A61B 17/0469; A61B 17/0487; A61F 2/24; A61F 2/2466; A61F 2/2445
See application file for complete search history.

(56) References Cited

U.S. PATENT DOCUMENTS

| 7,988,725 B2 | 2/2011 | Gross et al. |
| 9,132,009 B2 | 9/2015 | Hacohen et al. |
| 9,180,005 B1 | 11/2015 | Lashinski et al. |
| 9,241,702 B2 | 1/2016 | Maisano et al. |
| 2006/0135967 A1 | 6/2006 | Realyvasquez |
| 2008/0306586 A1 | 12/2008 | Cartledge et al. |

(Continued)

OTHER PUBLICATIONS

International Application # PCT/IB2017/052331 search report dated Sep. 12, 2017.

(Continued)

*Primary Examiner* — Vi X Nguyen
(74) *Attorney, Agent, or Firm* — Kligler & Associates

(57) ABSTRACT

Described embodiments include apparatus (20) that includes an assembly of tubes (34), each one of the tubes being shaped to define a tube lumen (62). The apparatus further includes a plurality of tissue anchors (60), each one of the tissue anchors being disposed within a respective one of the tube lumens, an expandable annular structure (36), including a plurality of teeth (40), coupled to the assembly of tubes, and a plurality of control wires (38) coupled to the annular structure, configured to position the tubes for deployment of the tissue anchors from the tube lumens, by manipulating the annular structure. Other embodiments are also described.

25 Claims, 16 Drawing Sheets

(56) References Cited

U.S. PATENT DOCUMENTS

| | | |
|---|---|---|
| 2010/0179648 A1 | 7/2010 | Richter et al. |
| 2012/0059458 A1 | 3/2012 | Buchbinder et al. |
| 2012/0245604 A1 | 9/2012 | Tegzes |
| 2012/0283757 A1 | 11/2012 | Miller et al. |
| 2013/0123910 A1 | 5/2013 | Cartledge et al. |
| 2013/0304197 A1 | 11/2013 | Buchbinder et al. |
| 2013/0331930 A1 | 12/2013 | Rowe et al. |
| 2014/0309730 A1* | 10/2014 | Alon .................. A61F 2/2409 623/2.11 |
| 2015/0173897 A1 | 6/2015 | Raanani et al. |
| 2015/0366556 A1 | 12/2015 | Khairkhahan et al. |
| 2016/0015515 A1 | 1/2016 | Lashinski et al. |

OTHER PUBLICATIONS

Bar, Eli et al ., Application # PCT/IB2018/050555 filed Jan. 30, 2018.

International Application # PCT/IB2018/050555 search report dated May 10, 2018.

* cited by examiner

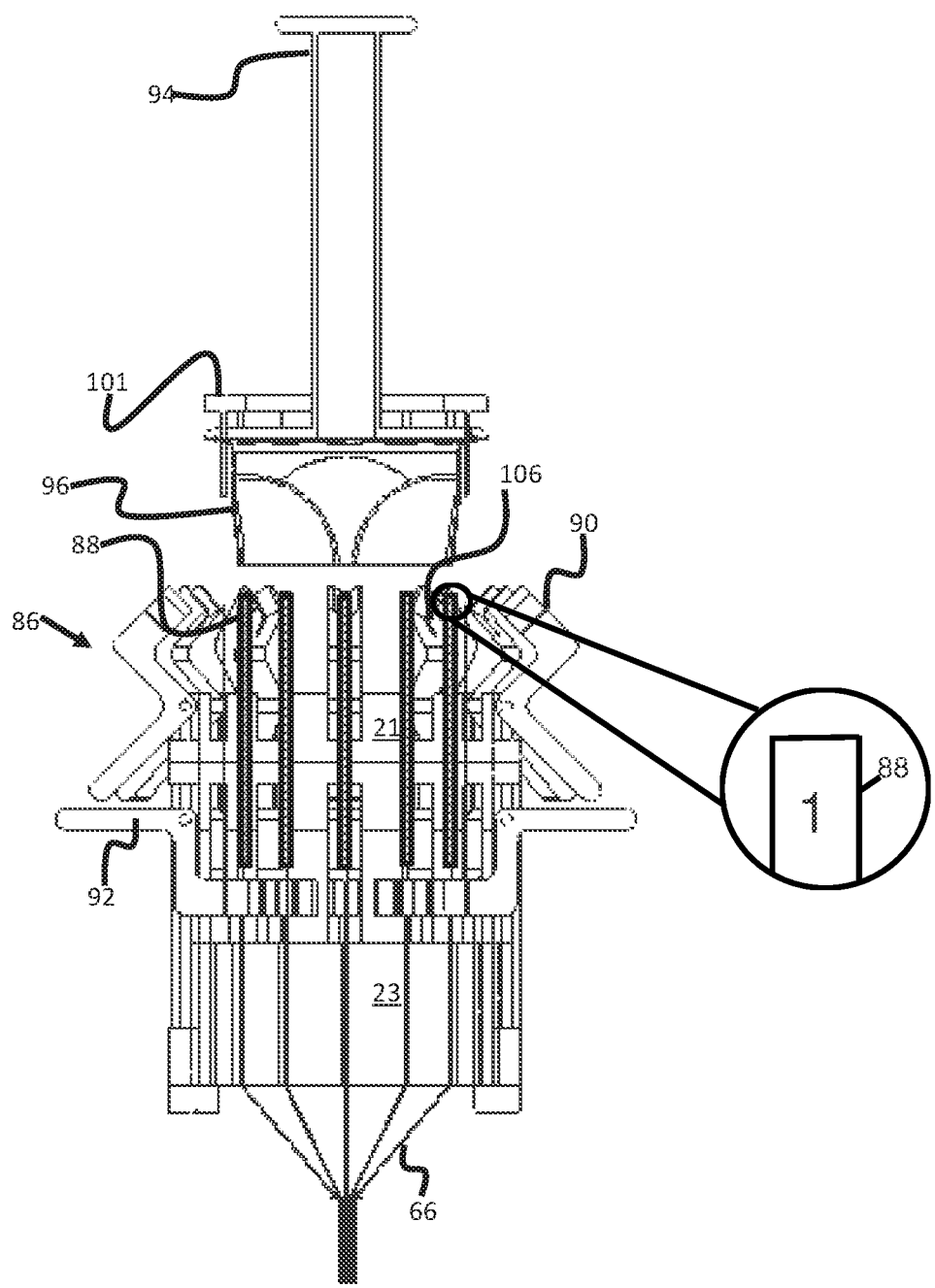

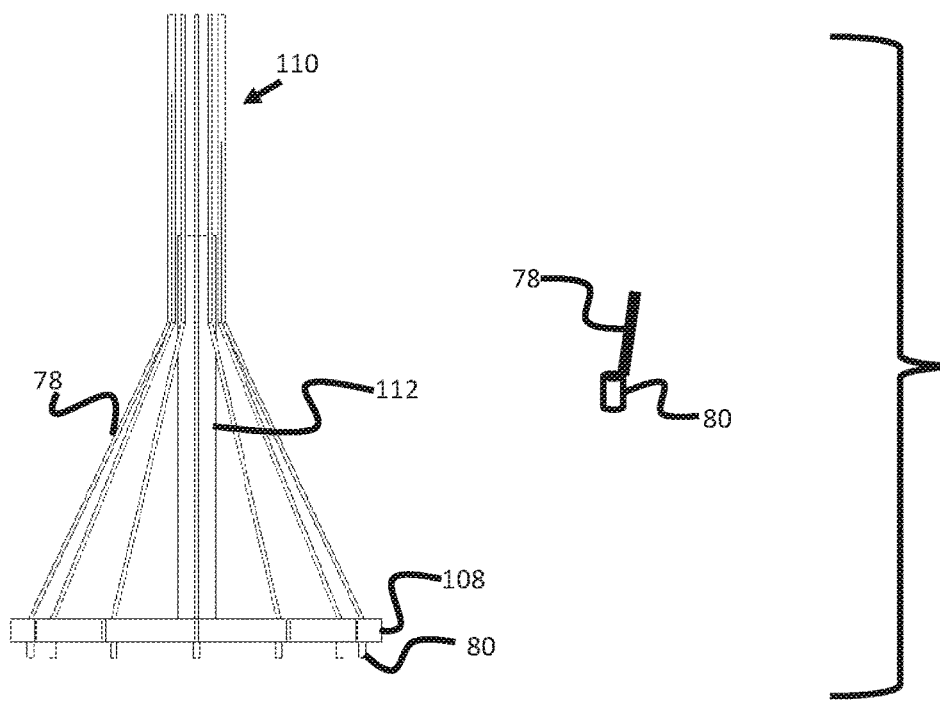

10,278,820 B2

PERCUTANEOUS VALVE REPAIR AND REPLACEMENT

CROSS-REFERENCE TO RELATED APPLICATIONS

The present application is a continuation of, and claims the benefit of, International Patent Application PCT/IB2017/052331 (published as WO/2017/187312), entitled "Percutaneous valve repair and replacement," filed Apr. 24, 2017, whose disclosure is incorporated herein by reference, which claims the benefit of (i) U.S. provisional application 62/327,176, entitled "System and method for percutaneous valve repair and replacement," filed Apr. 25, 2016, whose disclosure is incorporated herein by reference, (ii) U.S. provisional application 62/337,347, entitled "Percutaneous valve repair and replacement," filed May 17, 2016, whose disclosure is incorporated herein by reference, and (iii) U.S. provisional application 62/453,556, entitled "System and method for percutaneous valve repair and replacement," filed Feb. 2, 2017, whose disclosure is incorporated herein by reference.

FIELD OF THE INVENTION

Embodiments of the present invention relate generally to the field of medical devices, and particularly, to apparatus and methods for percutaneous valve repair and replacement.

BACKGROUND

In some subjects, an implant may be used to repair or replace an intracardiac valve. For example, a replacement valve and/or an annuloplasty ring may be used to repair a regurgitating mitral valve.

U.S. Pat. No. 9,132,009, whose disclosure is incorporated herein by reference, describes apparatus, including one or more valve support guide members configured to be delivered to one or more commissures of a native atrioventricular valve of a patient, one or more valve support anchors configured to be anchored to the one or more commissures of the native valve, a prosthetic valve support advanceable toward the native valve along the one or more valve support guide members and anchored to the native valve at least the one or more commissures, and a prosthetic valve configured to be coupled to the valve support. Other applications are also described.

US Patent Application Publication 2010/0179648, whose disclosure is incorporated herein by reference, describes a system and process for placing a percutaneous valve device in a body lumen at the location of implantation. Anchors and placement wires or sutures are used to fix the implantation target and guide the device to the implantation site. The system and method are applicable to pre-assembled percutaneous valve devices as well as a modular prosthetic valve device, which modular device is also provided. The modular valve device comprises two or more device modules and is designed to be delivered unassembled and then assembled in the body lumen at or near the site where implantation occurs. The device modules may be assembled before or after the implantation target is fixed with the anchor, and then placed using the placement system in a manner similar to how a pre-assembled percutaneous valve device may be placed in accordance with the invention.

US Patent Application Publication 2012/0283757, whose disclosure is incorporated herein by reference, describes apparatus for use with an implant configured to be coupled to cardiac tissue of a patient, the apparatus including: a tissue anchor including: a distal tissue coupling element configured to couple the tissue anchor to the cardiac tissue of the patient, and a proximal implant-receiving element configured to receive at least a portion of the implant and facilitate coupling of the implant to the tissue anchor. The proximal implant-receiving element includes an implant-restraining element coupled to a portion of the implant-receiving element, the implant-restraining element being configured to restrain the implant from separating from the implant-receiving element. Other applications are also described.

US Patent Application Publication 2012/0245604, whose disclosure is incorporated herein by reference, describes a device, kit and method that may include or employ an implantable device (e.g., annuloplasty implant) and a plurality of tissue anchors. The implantable device is positionable in a cavity of a bodily organ (e.g., a heart) and operable to constrict a bodily orifice (e.g., a mitral valve). Each of the tissue anchors may be guided into precise position by an intravascularly or percutaneously techniques. Constriction of the orifice may be accomplished via a variety of structures, for example an articulated annuloplasty ring, the ring attached to the tissue anchors. The annuloplasty ring may be delivered in an unanchored, generally elongated configuration, and implanted in an anchored generally arched, arcuate or annular configuration. Such may approximate the septal and lateral (clinically referred to as anterior and posterior) annulus of the mitral valve, to move the posterior leaflet anteriorly and the anterior leaflet posteriorly, thereby improving leaflet coaptation to reduce mitral regurgitation.

US Patent Application Publication 2006/0135967, whose disclosure is incorporated herein by reference, describes a valve delivery device and method of use. In one embodiment, the device to deliver a valve prosthesis to a target tissue may include at least one anchor and at least one guide wire coupled to the anchor. The device has a fastener housing. The device may also include a first set of fasteners in said fastener housing, wherein the fasteners are movable from a first position to a second, tissue engagement position. The device may also include a second set of fasteners housed in the anchor to attach the anchor to the tissue, wherein the fasteners are movable from a first position to a second, tissue engagement position. The guide wire may be slidably received in the fastener housing and has a length sufficient to extend from the fastener housing to the target tissue site, wherein the guide wire is used to direct the fastener housing into place.

US Patent Application Publication 2015/0366556, whose disclosure is incorporated herein by reference, describes a device for use in anchoring an implant, including anchors, sutures, implants, clips, tools, lassos, and methods of anchoring among other methods. Anchors as disclosed therein could be utilized to secure a coaptation assistance device, an annuloplasty ring, an artificial valve, cardiac patch, sensor, pacemaker, or other implants. The implant could be a mitral valve ring or artificial mitral valve in some embodiments.

SUMMARY OF THE INVENTION

There is provided, in accordance with some embodiments of the present invention, apparatus that includes an assembly of tubes, each one of the tubes being shaped to define a tube lumen. The apparatus further includes a plurality of tissue anchors, each one of the tissue anchors being disposed within a respective one of the tube lumens. The apparatus further includes an expandable annular structure coupled to the assembly of tubes, and a plurality of control wires coupled to the annular structure. The control wires are configured to position the tubes for deployment of the tissue anchors from the tube lumens, by manipulating the annular structure.

In some embodiments, the annular structure includes a plurality of teeth.

In some embodiments, each one of the teeth has a top vertex that is coupled to a respective one of the control wires.

In some embodiments, the plurality of teeth include:
a first annulus of teeth; and
a second annulus of teeth coupled to, and angled radially inward with respect to, the first annulus of teeth.

In some embodiments, the apparatus further includes a plurality of anchor-pushing elements disposed within the tube lumens, each one of the anchor-pushing elements being configured to deploy a respective one of the tissue anchors from a respective one of the tube lumens by pushing the respective one of the tissue anchors.

In some embodiments, each one of the tubes includes a pointed distal end.

In some embodiments, the pointed distal end is curved radially inward.

In some embodiments, the apparatus further includes a plurality of threads, each thread of the threads passing through a respective one of the tube lumens and being coupled, at a distal end of the thread, to a respective one of the tissue anchors.

In some embodiments, each of the threads passes at least partly through a respective one of the tube lumens.

In some embodiments, the apparatus further includes a plurality of loading rods, each thread of the threads being coupled, at a proximal end of the thread, to a respective one of the loading rods.

In some embodiments, at least some of the tissue anchors include respective tissue-anchor markers that are different from each other, and at least some of the loading rods include respective loading-rod markers that are different from each other, such that the tissue-anchor markers and the loading-rod markers collectively indicate, for each loading rod of the loading rods, the tissue anchor to which the loading rod, via one of the threads, is coupled.

In some embodiments, the apparatus further includes a loading shaft, configured to load an implant, which is mounted on the loading shaft, onto the loading rods.

In some embodiments, the apparatus further includes a loading chamber configured to facilitate a loading of an implant onto the loading rods by holding the loading rods within the loading chamber.

In some embodiments, the loading chamber is further configured to crimp the implant, following the loading of the implant onto the loading rods.

In some embodiments, the apparatus further includes a plurality of locking elements, each locking element of the locking elements being shaped to define one or more apertures, and being configured to lock an implant in place at an implantation site following deployment of the tissue anchors at the implantation site and advancement of the implant over the threads to the implantation site, by virtue of (i) a respective one of the threads being looped through the apertures such that the locking element cannot move proximally over the respective one of the threads, and (ii) the locking element being positioned against the implant.

There is further provided, in accordance with some embodiments of the present invention, a method that includes deploying, from a catheter, an expandable annular structure that is coupled to an assembly of tubes and to a plurality of control wires. The method further includes, for each tube of the tubes, using one or more of the control wires, adjusting a position of the tube by manipulating the annular structure. The method further includes, subsequently, deploying a respective tissue anchor from a lumen of the tube.

In some embodiments, adjusting the position of the tube includes adjusting the position of the tube independently from positions of other ones of the tubes.

In some embodiments, deploying the expandable annular structure includes deploying the expandable annular structure within a chamber of a heart.

In some embodiments, the method further includes, for each tube of the tubes, prior to deploying the respective tissue anchor, passing a distal end of the tube through tissue.

In some embodiments, passing the distal end of the tube through the tissue includes passing the distal end of the tube through tissue of an annulus of a valve of a heart such that the tube emerges from the tissue at an anchoring site on a radially-inward-facing face of the annulus, and deploying the respective tissue anchor includes deploying the respective tissue anchor at the anchoring site.

In some embodiments, the anchoring site is within an atrium of the heart.

In some embodiments, the anchoring site is within a ventricle of the heart.

In some embodiments, the method further includes, subsequently to deploying the tissue anchors, advancing an implant to an implantation site over threads that are coupled, at respective distal ends of the threads, to the tissue anchors.

In some embodiments, the method further includes, using a plurality of locking elements, locking the implant in place at the implantation site, by:
looping a respective one of the threads through one or more apertures of each locking element of the locking elements, such that the locking element cannot move proximally over the respective one of the threads, and
subsequently, advancing the locking elements over the threads such that the locking elements are positioned against the implant at the implantation site.

In some embodiments, the implant includes an annuloplasty ring including a plurality of separable segments shaped to define a plurality of apertures, and advancing the implant includes:
passing the threads through the apertures; and
subsequently, advancing the segments of the ring, separately from each other, over the threads.

In some embodiments, the method further includes, subsequently to advancing the segments of the ring over the threads, reassembling the ring by tightening an adjustment chord that passes through the ring.

In some embodiments, each thread of the threads is coupled, at a proximal end of the thread, to a respective loading rod, and the method further includes, prior to advancing the implant over the threads, loading the implant onto the loading rods.

In some embodiments,
at least some of the tissue anchors include respective tissue-anchor markers that are different from each other,
at least some of the loading rods include respective loading-rod markers that are different from each other, and
the method further includes, prior to loading the implant onto the loading rods:
acquiring at least one image of the tissue-anchor markers, and responsively to the image and to the loading-rod markers, aligning the implant with respect to the loading rods.

There is further provided, in accordance with some embodiments of the present invention, apparatus for implantation over an annulus of a valve of a heart of a subject, the apparatus including:

an annuloplasty ring including a plurality of separable segments shaped to define a plurality of apertures, the segments being configured to advance to the valve, separately from each other, over threads passing through the apertures; and an adjustment chord passing through the ring, the adjustment chord being configured to reassemble the ring at the valve upon being tightened.

In some embodiments, the apparatus further includes a plurality of magnets at respective ends of the segments, the magnets being configured to facilitate the reassembly of the ring by virtue of each one of the magnets attracting another one of the magnets.

The present invention will be more fully understood from the following detailed description of embodiments thereof, taken together with the drawings, in which:

BRIEF DESCRIPTION OF THE DRAWINGS

FIG. 8 is a schematic illustration of a loading chamber, in accordance with some embodiments of the present invention;

FIG. 9 is a schematic illustration of an implant advancer, in accordance with some embodiments of the present invention;

DETAILED DESCRIPTION OF EMBODIMENTS

Overview

Figure 1:
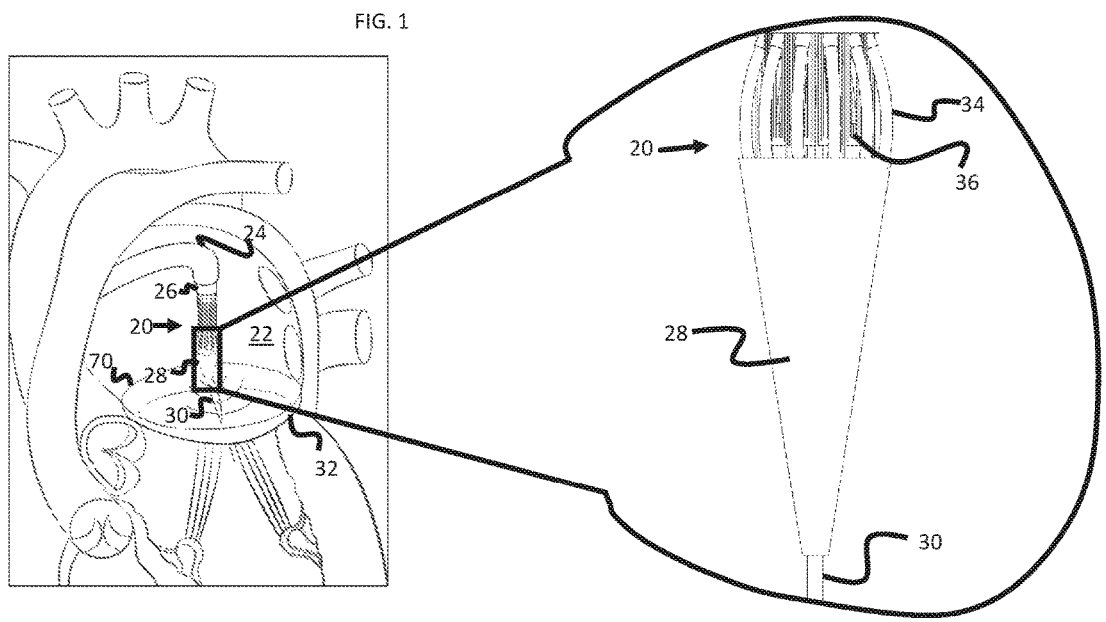
FIG. 1 is a schematic illustration showing the deployment of an anchor-deployment apparatus into a left atrium of a subject, in accordance with some embodiments of the present invention.

Embodiments described herein include apparatus and methods for facilitating the percutaneous implantation of an implant at an implantation site. For example, embodiments described herein may be used for facilitating the percutaneous implantation of an annuloplasty ring and/or a replacement valve inside the heart, to repair or replace a mitral valve or tricuspid valve.

First, an anchor-deployment apparatus is used to deploy a plurality of anchors at the implantation site. The anchor-deployment apparatus comprises an assembly of tubes and a plurality of tissue anchors, each one of the tissue anchors being disposed within a respective one of the tubes. The anchor-deployment apparatus further comprises an expandable annular structure coupled to the assembly of tubes, and a plurality of control wires coupled to the annular structure. The control wires are used to adjust the respective positions of the tubes. Subsequently, the tissue anchors are deployed from the tubes, and are anchored at the implantation site.

Each of the tissue anchors is coupled to a respective thread, which passes from the tissue anchor to the exterior of the subject. Following the anchoring of the tissue anchors, an implant is loaded onto the threads, and is subsequently advanced along the threads to the implantation site. Embodiments described herein include a loading shaft and loading chamber for loading the implant onto the threads, and an implant advancer for advancing the implant along the threads.

Advantages of embodiments described herein include at least the following:

(i) The anchors, and implant, may be delivered percutaneously, using a minimally-invasive approach.

(ii) Due to the tissue anchors being separate from the implant, the implant may be smaller, and/or have a simpler profile, than would otherwise be possible if the anchors were an integral part of the implant. Moreover, if a first implant (e.g., an annuloplasty ring) does not achieve the desired effect, the first implant may be withdrawn without removing the anchors, and a second implant (e.g., a replacement valve) may then be passed over the threads. Alternatively, the second implant may be implanted as a complement to the first implant, without the need to deploy any additional anchors at the implantation site.

(iii) The anchor-deployment apparatus facilitates a precise placement of the anchors at the implantation site, in that the respective positions of the tubes may be precisely adjusted prior to deployment of the anchors. Embodiments described herein allow each tube to be positioned individually, i.e., independently from the other tubes.

(iv) As further described below, the tissue anchors are typically anchored on the surface of the radially-inward-facing face of the valve annulus, rather than within the tissue of the valve annulus. This allows the threads to be pulled taut, without risking uprooting the anchors. The pulling of the threads, in turn, may facilitate holding the anchors in place, delivering the implant to the implantation site, and/or locking the implant in place at the implantation site.

(v) As further described below, markers on the tissue anchors may be used to guide the delivery of the implant. In particular, the markers may allow the implant to be loaded onto the threads such as to optimize the fit between the implant and the implantation site.

(vi) By virtue of the implant being delivered over the threads, the valve annulus conforms to the shape of the implant. Thus, for example, the circumference of the implant may be made smaller than the natural circumference of the valve annulus, and, as the implant approaches the valve, the valve annulus will be drawn inward, to conform to the shape of the implant.

(vii) It may be possible to deliver an annuloplasty ring to the implantation site without needing to first crimp the annuloplasty ring, as described below with reference to FIGS. 13A-B.

Apparatus Description

Reference is initially made to FIG. 1, which is a schematic illustration showing the deployment of an anchor-deployment apparatus 20 into a left atrium 22 of a subject, in accordance with some embodiments of the present invention. As described in detail below, apparatus 20 is used to anchor a plurality of tissue anchors at an implantation site, such as a mitral valve annulus 70 of a mitral valve 32, such as to facilitate the subsequent implantation of an implant at the implantation site.

Typically, apparatus 20 is introduced into left atrium 22 while contained inside a catheter 26, contained, in turn, inside a sheath 24. Typically, sheath 24 is percutaneously inserted into the heart, e.g., via the femoral vein and inferior vena cava, or via the jugular vein and superior vena cava. Sheath 24 is typically advanced over a guidewire 30, under fluoroscopic guidance, and/or under the guidance of any other suitable imaging modality, such as ultrasound (e.g., transthoracic echocardiography (TTE) or transesophageal echocardiography (TEE)), magnetic resonance imaging (MRI), or computed tomography (CT). Techniques known in the art are used to pass the sheath through the interatrial septum and into the left atrium.

Apparatus 20 comprises an assembly of tubes 34, which may be manufactured from any suitable material, e.g., any suitable metal or plastic material. As further described below with reference to FIG. 4, each one of tubes 34 is shaped to define a tube lumen, within which a respective tissue anchor is disposed. Typically, the tubes pass through the entire length of catheter 26, such that, throughout the delivery, deployment, and subsequent use of apparatus 20, the proximal ends of tubes 34 are positioned outside of the subject.

Apparatus 20 further comprises an expandable annular structure 36 coupled to the assembly of tubes 34, at the distal end of the tube assembly. Annular structure 36 is typically manufactured from a suitable shape-memory material, e.g., nitinol. Prior to the full deployment of apparatus 20, annular structure is radially confined by (i) catheter 26, at least at the proximal end of the annular structure, and (ii) a retaining tip 28, at the distal end of the annular structure. Upon the distal end of sheath 24 being positioned within a suitable distance of mitral valve annulus 70, the distal end of catheter 26, containing the annular structure, is pushed out of the sheath. Subsequently, (i) the catheter is retracted from over the annular structure, and/or the annular structure is pushed out of the catheter, and (ii) retaining tip 28 is pushed off from the distal end of the annular structure, using a retaining-tip pushing element (not shown) that passes through catheter 26 from the exterior of the subject. The annular structure then radially expands from the radially-confined configuration shown in FIG. 1 to a preconfigured, radially-expanded configuration, such as that shown in FIG. 2, which is described immediately below. As the annular structure expands, the annular structure pushes out the distal ends of the tubes, such that the distal ends of the tubes also adopt a radially-expanded configuration.

Figure 2:
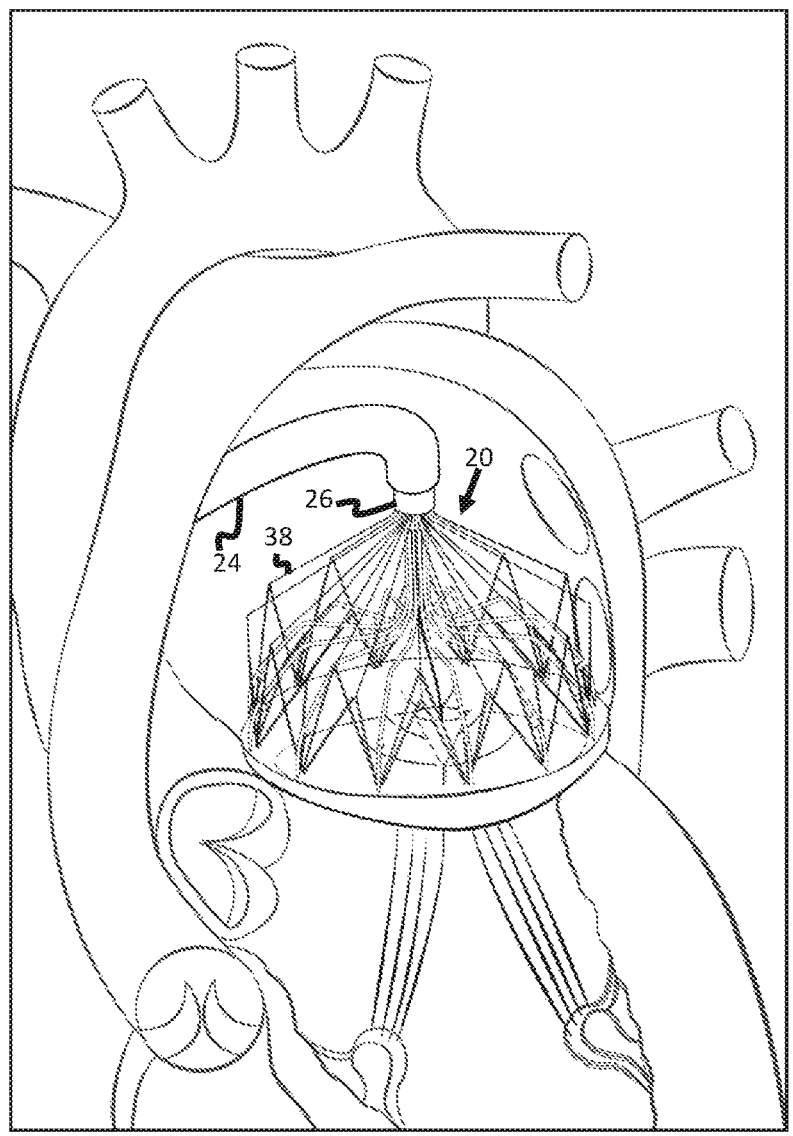
FIG. 2 is a schematic illustration of an anchor-deployment apparatus deployed within a left atrium, in accordance with some embodiments of the present invention.

In some embodiments, rather than opening the annular structure (i.e., causing the annular structure to radially expand) over the mitral valve annulus, the annular structure is opened beneath the mitral valve annulus, within the left ventricle, and is then retracted through the mitral valve annulus to the position shown in FIG. 2.

Reference is now made to FIG. 2, which is a schematic illustration of anchor-deployment apparatus 20 deployed within left atrium 22, in accordance with some embodiments of the present invention. As described above, upon retraction of the catheter and removal of the retaining tip, annular structure 36 expands radially outward, thus assuming the configuration shown in FIG. 2.

Apparatus 20 comprises a plurality of control wires 38, which are coupled to the annular structure. Typically, control wires 38 run through the entire length of catheter 26, and are connected, at their respective proximal ends, to a control handle. Using the control handle, the control wires may be used to manipulate the annular structure, thus—given the coupling of the annular structure to the tube assembly— positioning the tubes for deployment of the tissue anchors from the tube lumens. Typically, such positioning is performed under the guidance of a suitable imaging modality, such as fluoroscopy, and/or any of the other modalities mentioned above. In some embodiments, control wires 38, and/or tubes 34, comprise markers (e.g., radiopaque markers), which may facilitate the guiding of the tubes to the desired anchoring sites. The tubes may be positioned individually (i.e., the position of each tube may be adjusted independently from the positions of other tubes), or together.

Apparatus 20 will now be described in more detail, with reference being made to FIGS. 3A-B, which are schematic illustrations of anchor-deployment apparatus 20, in accordance with some embodiments of the present invention. In particular, FIG. 3A is a side view of, and FIG. 3B is an overhead view of, the radially-expanded distal end of apparatus 20.

Typically, annular structure 36 comprises a plurality of teeth 40. In some embodiments, as shown in FIGS. 3A-B, each tooth 40 has a top vertex 42, and two bottom vertices 44, at each of which the tooth is joined to a respective neighboring tooth, e.g., by being connected to a common joint 58. In such embodiments, control wires 38 are typically coupled to top vertices 42, and the control wires are used to manipulate the annular structure by applying appropriate forces to the teeth. (Although, for simplicity, FIGS. 3A-B each show only two control wires, it is noted that, typically, each of the teeth of the annular structure is coupled to a control wire.)

Figure 3A:
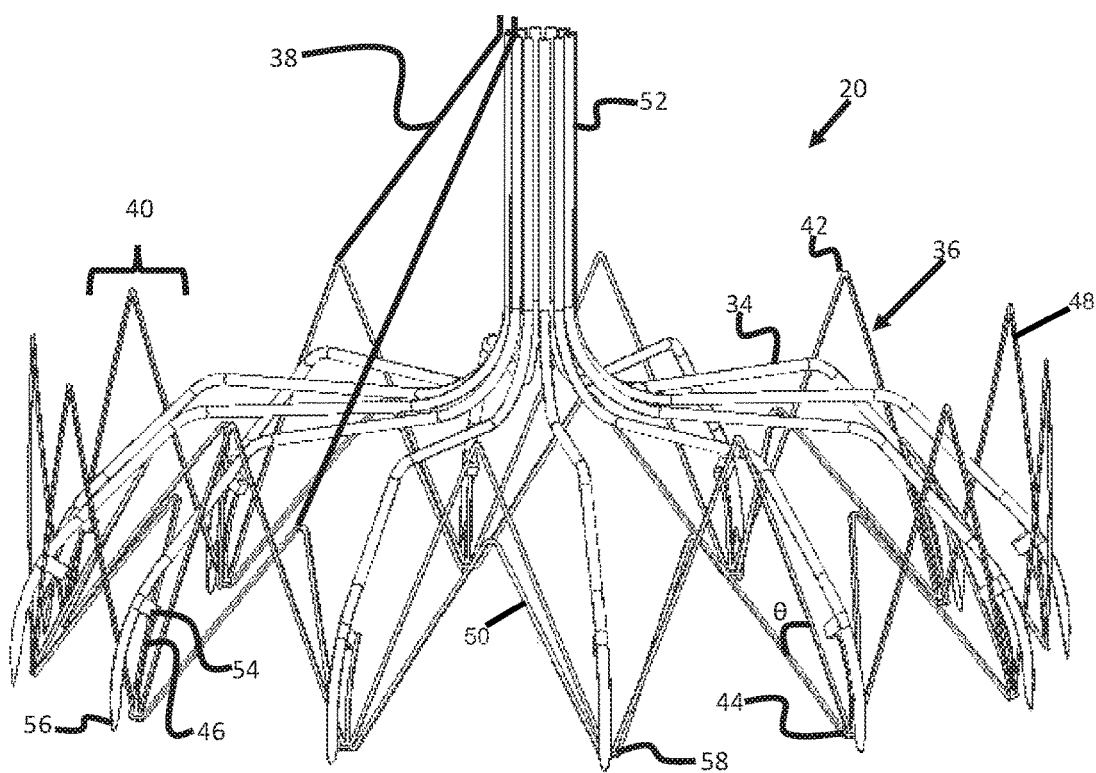
FIGS. 3A-B are schematic illustrations of an anchor-deployment apparatus, in accordance with some embodiments of the present invention.
Figure 3B:
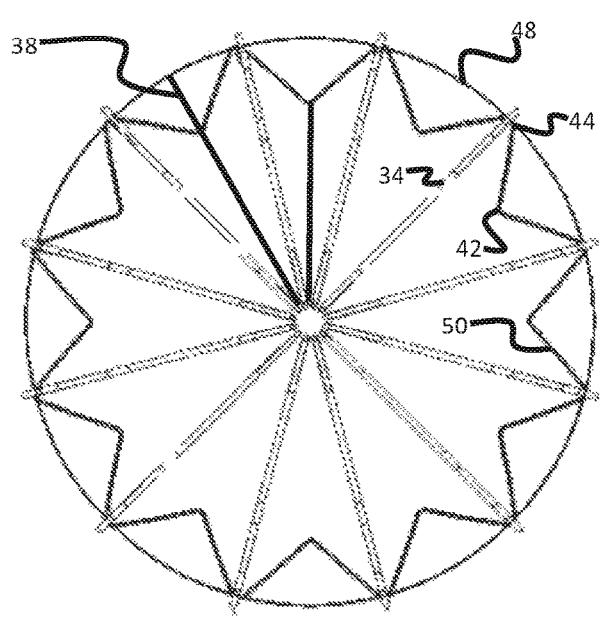

In some embodiments, as shown in FIGS. 3A-B, annular structure 36 comprises two annuli of teeth, which are coupled to one another. Typically, the teeth of the first, outer annulus 48 stand approximately upright. That is, for each tooth belonging to outer annulus 48, the angle between (i) a hypothetical flat, horizontal surface on which the annular structure stands, and (ii) a hypothetical plane that contains the top vertex and two bottom vertices of the tooth, is approximately 90 degrees, e.g., between 80 and 100 degrees.

Stated differently, the hypothetical plane is approximately parallel to the "axis" 52 that is defined by the assembly of tubes 34 proximally to the annular structure. The control wires coupled to outer annulus 48 may thus be used to apply an upward or downward, i.e., "axial," force to the annular structure. The application of a downward force, for example, may help bring the annular structure closer to the mitral valve annulus, and/or stabilize the annular structure against the mitral valve annulus while the tissue anchors are deployed from the tubes.

The second, inner annulus 50 is typically angled radially inward with respect to outer annulus 48. For example, as shown in FIGS. 3A-B, each tooth belonging to inner annulus 50 may be coupled to a respective tooth belonging to outer annulus 48, the inner tooth leaning inward from the outer tooth such that, for example, the angle theta (θ) between the inner tooth and the outer tooth is between 10 and 90 degrees, such as between 40 and 50 degrees (e.g., 45 degrees), or greater than 90 degrees. As shown, the inner tooth may be coupled to the outer tooth at two neighboring joints 58; at each of the two neighboring joints 58, a respective bottom vertex 44 of the inner tooth is coupled to a respective bottom vertex of the outer tooth. (Thus, at each joint 58, a total of four bottom vertices are coupled to each other.)

Due to the inward angling of inner annulus 50, the control wires coupled to inner annulus 50 may be used to apply a radially-outward ("pushing") or radially-inward ("pulling") force to the annular structure, thus adjusting the radial extent of the annular structure.

It follows that, typically, for the embodiment shown in FIGS. 3A-B, one or more of a plurality of control wires may be used to position each tube, and/or stabilize the annular structure in the vicinity of the tube. This plurality of control wires typically include at least (i) the two control wires coupled, respectively, to the two outer teeth that neighbor the tube, respectively, on each side of tube, and (ii) the two control wires coupled, respectively, to the two inner teeth that neighbor the tube, respectively, on each side of tube.

As shown in FIG. 3A, each one of the tubes typically comprises a pointed distal end 56. (Thus, each tube may be said to comprise a "needle." For example, the distal end of each tube may be referred to as a needle, or each tube may itself be referred to as a needle.) Upon the tube being appropriately situated, pointed distal end 56 is passed through the tissue of the mitral valve annulus, prior to deploying a tissue anchor from the tube, as further described below with reference to FIG. 6. Typically, as shown, the distal end of each tube is curved radially inward, such that, as further described below with reference to FIG. 6, pointed distal end 56 may enter the mitral valve annulus through the top face of the annulus, and exit the mitral valve annulus through the radially-inward-facing face of the mitral valve annulus.

Typically, each tube is flexible over the majority of the length of the tube, to facilitate the bending of the tube as it passes through the vasculature of the subject. The pointed distal end of the tube, on the other hand, is typically more rigid (i.e., less flexible), to facilitate the puncturing of tissue by the pointed distal end. (The distal end of the tube may comprise, for example, the distalmost 5-20 mm of the tube.)

Typically, each tube is coupled to annular structure 36 via a tube support 46, which extends upward from joint 58. Tube support 46 comprises a tube guide 54, through which tube 34 may slide. For example, to drive pointed distal end 56 into tissue, the tube may be slid distally through tube guide 54. Conversely, to retract the pointed distal end (e.g., following the deployment of the anchor from the tube, or in the event that an adjustment to the position of the distal end is needed), the tube may be slid proximally through the tube guide. In some embodiments, pointed distal end 56 is screwed into tissue, by rotating the tube around its longitudinal axis while pushing the tube through the tube guide.

Figure 4:
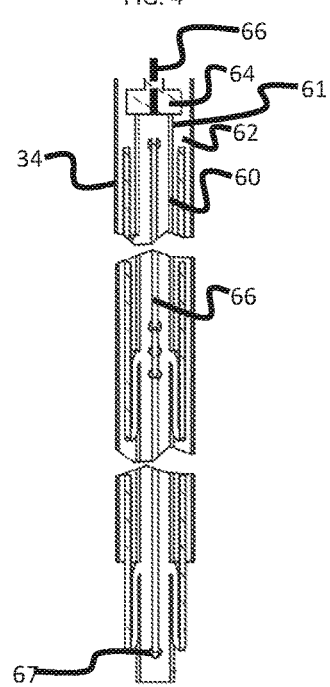
FIG. 4 is a schematic illustration of a longitudinal cross-section through the distal end of a tube, in accordance with some embodiments of the present invention.
Figure 5A:
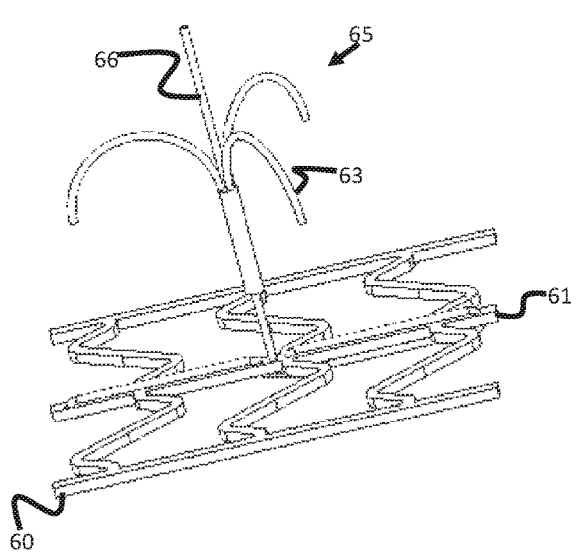
FIG. 5A is a schematic illustration of a tissue anchor, in accordance with some embodiments of the present invention.

Reference is now made to FIG. 4, which is a schematic illustration of a longitudinal cross-section through the distal end of a tube 34, in accordance with some embodiments of the present invention, and to FIG. 5A, which is a schematic illustration of a tissue anchor 60, in accordance with some embodiments of the present invention.

As shown in FIG. 4, each tube 34 is shaped to define a tube lumen 62, within which is disposed a tissue anchor 60, i.e., each tube contains a respective tissue anchor 60. Tissue anchor 60 is typically manufactured from a suitable shape-memory material, such as nitinol. While contained inside of the tube, tissue anchor 60 is held in a closed, or confined, configuration. Upon being pushed from the tube, the tissue anchor expands, thus assuming a preconfigured open configuration, such as that shown in FIG. 5A. Typically, each tube 34 contains an anchor-pushing element 64, which passes through catheter 26 and the tube, from the exterior of the subject. Anchor-pushing element 64 is used to push the tissue anchor from the tube. (FIG. 4 shows the anchor beginning to emerge from the tube, due to being pushed by the anchor-pushing element.) Typically, at least the distal end of anchor-pushing element 64 is hollow, i.e., at least the distal end of anchor-pushing element 64 is shaped to define a lumen thereof.

As shown in FIGS. 4 and 5A, each tissue anchor (e.g., at the central shaft 61 of the tissue anchor) is coupled to a respective thread 66. (In the context of the present application, including the claims, the term "thread" may include within its scope any flexible longitudinal element, such as a string, wire, or chord.) Typically, from the anchor, thread 66 (i) passes through the lumen of the anchor-pushing element, (ii) exits the lumen of the anchor-pushing element and the lumen of the tube, (iii) via an opening in the wall of catheter 26 (which may be referred to as a "rapid exchange portion"), exits from catheter 26, and (iv) runs, within sheath 24, to the exterior of the subject. (Notwithstanding the above, it is noted that thread 66 may pass only partly through the lumen of the tube, or not through the lumen of the tube at all. For example, thread 66 may run alongside the tube, alternatively or additionally to passing through the lumen of the tube.) Thus, the distal end of each thread is coupled to the tissue anchor, and the proximal end of the thread is outside of the subject, such that, as further described below, following the anchoring of the anchors, an implant may be advanced over the threads, for implantation at the implantation site.

In some embodiments, as shown in FIG. 5A, a retainer 65 is coupled to thread 66, proximally to the tissue anchor. As further described below with reference to FIG. 6, retainer 65 helps prevent the tissue anchor from migrating from the mitral valve annulus, by engaging with the tissue of the mitral valve annulus. In some embodiments, retainer 65 comprises a plurality of prongs 63, which project radially outward from thread 66. Such prongs may be straight, or arced toward the anchor, as shown. Prongs 63 may be of any suitable number; for example, FIG. 5A shows in embodiment in which retainer 65 comprises three prongs. Typically, retainer 65 is manufactured from a suitable shape-memory material, such as nitinol. Prior to being released, the retainer is held in a confined configuration within the lumen of the anchor-pushing element. Subsequently, upon being released, as described below with reference to FIG. 6, the retainer opens up to its preconfigured open configuration.

Figure 5B:
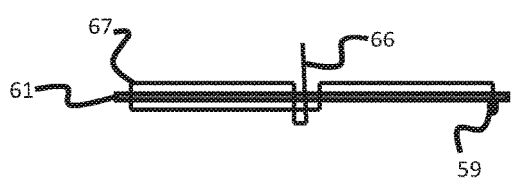
FIG. 5B is a schematic illustration of a locked central shaft of a tissue anchor, in accordance with some embodiments of the present invention.

Reference is now made to FIG. 5B, which is a schematic illustration of a locked central shaft 61 of a tissue anchor, in accordance with some embodiments of the present invention.

In some embodiments, thread 66 loops through one or more apertures 67 in the tissue anchor. For example, the thread may loop through one or more apertures 67 in central shaft 61 of the tissue anchor, following the path shown in FIG. 5B, or following any other suitable path. The distal tip of the thread may be coupled to a stopper 59, such as a bead, which prevents the thread from sliding backward through the apertures. Following the deployment of the anchor at the implantation site, thread 66 is pulled, thus causing the loops to be tightened. The tightening of the loops locks the anchor in the open position at the implantation site, such that forces applied to the anchor by the mitral valve do not cause the anchor to buckle.

Figure 6:
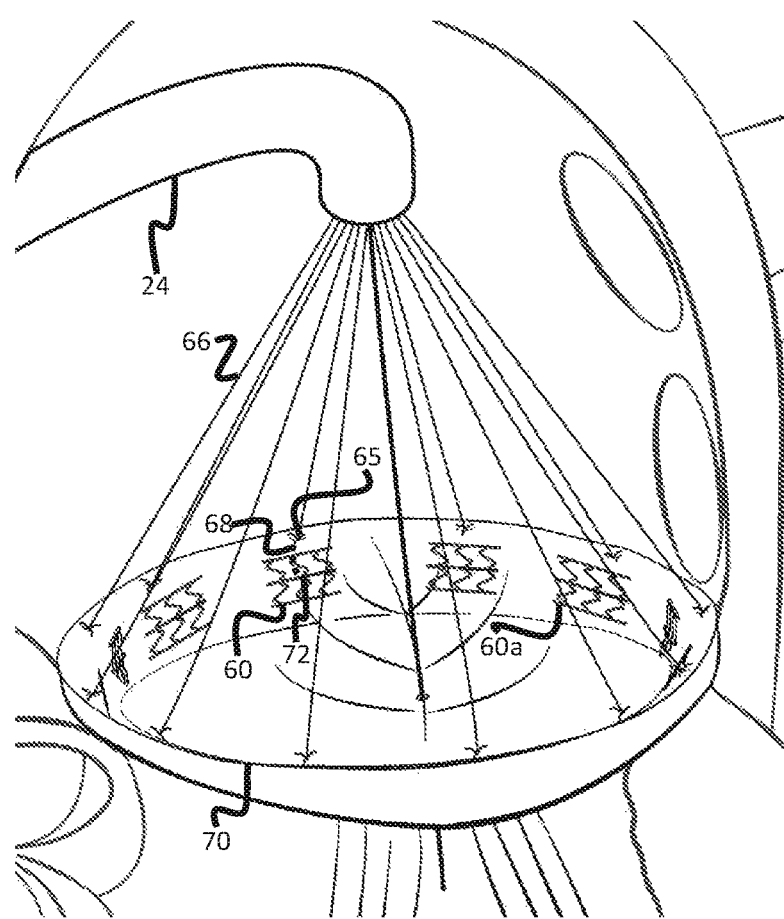
FIG. 6 is a schematic illustration of a plurality of tissue anchors anchored to a mitral valve annulus, in accordance with some embodiments of the present invention.

Reference is now made to FIG. 6, which is a schematic illustration of a plurality of tissue anchors 60 anchored to a mitral valve annulus 70, in accordance with some embodiments of the present invention.

As described above, control wires 38 are used to position the tubes for deployment of the tissue anchors. For example, each tube may be moved to an appropriate proximal anchoring site 68 on the top face of mitral valve annulus 70. Upon a particular tube being appropriately positioned, the tube is passed through the tissue of mitral valve annulus 70, such that the tube enters the tissue at proximal anchoring site 68, and emerges from the tissue at a distal anchoring site 72. Typically, as described above with reference to FIG. 3A, the distal portion of each tube 34 is curved radially inward, such that, as shown in the figure, the tube emerges from the tissue at the radially-inward-facing face of the mitral valve annulus, i.e., distal anchoring site 72 is on the radially-inward-facing face of the mitral valve annulus. Distal anchoring site 72 may be above or beneath the leaflets of the valve, i.e., the distal anchoring site may be located within the left atrium or the left ventricle of the heart.

Subsequently to passing the tube through the tissue, the tissue anchor is pushed from the tube, using the anchor-pushing element. As described above with reference to FIGS. 4 and 5A-B, the anchor then opens. Subsequently, while the thread is pulled taut, the tube and the anchor-pushing element are retracted back through the tissue and from over retainer 65, causing retainer 65 to open at proximal anchoring site 68. Retainer 65 causes anchor 60 to remain at distal anchoring site 72, by engaging with the tissue of the mitral valve annulus at proximal anchoring site 68. Alternatively or additionally, anchors 60 may be held in place until after the implant procedure is complete, by virtue of a continuous pulling force being exerted on threads 66.

In some embodiments, the tubes penetrate the tissue only after all of the tubes are appropriately positioned. In other embodiments, at least one of the tubes may penetrate the tissue before all of the tubes are appropriately positioned. For example, the sequence of (i) positioning the tube, (ii) passing the tube through the mitral valve annulus, (iii) passing the tissue anchor from the tube, and (iv) retracting the tube, may be performed one tube at a time, for each of the tubes.

Subsequently to anchoring all of the tissue anchors, the tube assembly and the annular structure are withdrawn into catheter 26, and catheter 26 is then withdrawn from the body of the subject, leaving behind tissue anchors 60 and threads 66.

Typically, as the tubes are withdrawn, anchor-pushing elements 64 are held such that they partly protrude from the tubes; this helps prevent the pointed distal ends of the tubes from tearing the threads.

Figure 7:
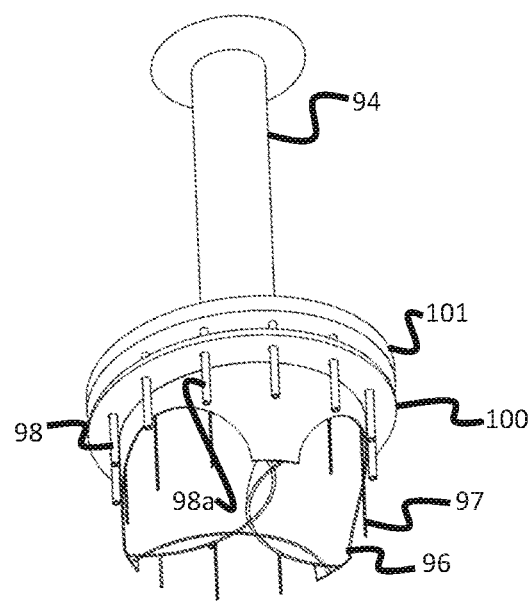
FIG. 7 is a schematic illustration of a loading shaft, in accordance with some embodiments of the present invention.

Reference is now made to FIG. 7, which is a schematic illustration of a loading shaft 94, in accordance with some embodiments of the present invention, and to FIG. 8, which is a schematic illustration of loading chamber 86, in accordance with some embodiments of the present invention. As described in detail below, loading shaft 94 and loading chamber 86 are used, in some embodiments, to load an implant onto the threads.

As shown in FIG. 8, typically, each thread 66 is coupled, at the proximal end of the thread (which is outside the body of the subject), to a respective loading rod 88. (For clarity, loading rods 88 are shown in FIG. 8 with a slightly exaggerated diameter, and with an overlaid pattern.) Each loading rod 88 may comprise, for example, a hollow tube, the proximal end of a thread 66 being fastened to the interior or exterior surface of the hollow tube. Alternatively, one or more of the loading rods may have a solid cross-section, the proximal ends of respective threads 66 being fastened to the exteriors of these loading rods.

Typically, at least some of the tissue anchors comprise respective tissue-anchor markers (not shown) that are different from each other, and at least some of the loading rods comprise respective loading-rod markers (not shown) that are different from each other, such that the tissue-anchor markers and the loading-rod markers collectively indicate, for each loading rod, the tissue anchor to which the loading rod, via one of the threads, is coupled. For example, there may be 12 tissue anchors, having, respectively, the tissue-anchor markers "1," "2," "3," . . . "12." (Such tissue-anchor markers may, for example, be radiopaque, such that they are visible under fluoroscopy.) In such an instance, the loading rod at the proximal end of the thread that is joined to anchor "1" may also be marked "1," the loading rod at the proximal end of the thread that is joined to anchor "2" may also be marked "2," etc. Alternatively, the loading-rod markers may correspond to the tissue-anchor markers in any other suitable way. For example, the loading rods may be marked "2," "4," "6," . . . "24," or, alternatively, "A," "B," "C," . . . "L." In general, the tissue anchors, and the loading rods, may be marked in any suitable way (e.g., using dots, dashes, and/or other symbols, and/or using alphanumeric markers, as described above), as long as it is clear, from the markings, which of the loading rods is connected to each particular tissue anchor.

When loading the implant onto the loading rods, the loading rods are arranged in the order matching that of the tissue anchors, such that, for any given loading rod, the two neighbors of the loading rod are connected, respectively, to the two tissue anchors that neighbor the tissue anchor to which the loading rod is connected. Thus, for example, if tissue anchors "1" through "12" are sequentially arranged in a clockwise orientation around the mitral valve annulus, loading rods "1" through "12" will also be sequentially arranged in a clockwise orientation, during the loading of the implant. It is noted that, as long as the ordering of the loading rods always matches that of the tissue anchors, as described above, it may not be necessary to mark each of the tissue anchors, or each of the loading rods. For example, it may be sufficient to mark three of the tissue anchors, and three of the loading rods.

In some embodiments, loading shaft 94 is used to load the implant onto the loading rods. First, the implant is mounted onto the loading shaft. Loading shaft 94 typically comprises a plurality of hollow mounting rods 98, onto which the implant is mounted. Typically, the number of mounting rods matches that of the loading rods, and each of the mounting rods is aligned with a respective loading rod. Moreover, typically, for each aligned mounting-rod-and-loading-rod pair, the cross-sectional shape of the mounting rod matches that of the loading rod, and the cross-sectional area of the mounting rod is slightly greater than that of the loading rod. Hence, the implant may be loaded onto the loading rods by virtue of the mounting rods and loading rods mating with each other, i.e., by virtue of each of the loading rods passing through a respective one of the mounting rods.

Typically, prior to loading the implant, at least one image of the tissue-anchor markers is acquired. (Such an image have been acquired during the deployment of the tissue anchors.) The tissue-anchor markers, being distributed along the mitral valve annulus, delineate the shape of the mitral valve annulus, such that, in response to viewing the image of the tissue-anchor markers, the operating physician may decide how to best align the implant with the mitral valve annulus. With additional reference to the loading-rod markers, the implant may then be aligned with respect to the loading rods such that this "best match" is achieved.

For example, FIG. 7 shows a replacement valve 96 mounted on the loading shaft, by virtue of mounting rods 98 passing through the annulus 100 of replacement valve 96. Assuming that—as is typically the case—the shape of annulus 100 of the replacement valve and the shape of the natural mitral valve annulus are both asymmetrical, the pairwise alignment between the mounting rods and the loading rods may affect the goodness of the fit between the replacement valve and the mitral valve annulus. Hence, as described above, the operating physician may refer to an image of the tissue-anchor markers, in order to ascertain the best pairwise alignment between the mounting rods and the loading rods. Thus, for example, in response to viewing the image, the physician may ascertain that the best fit will be achieved if the portion of the replacement valve mounted onto a particular mounting rod 98*a* is implanted over the portion of the mitral valve annulus to which a particular tissue anchor 60*a* (FIG. 6) is anchored. The physician may therefore load the replacement valve such that mounting rod 98*a* mates with the loading rod coupled—via a thread 66—to tissue anchor 60*a*.

In some embodiments, the loading shaft comprises loading-shaft markers that indicate a predetermined desired loading orientation of the implant. Such markers may be disposed, for example, on the base 101 of the loading shaft to which mounting rods 98 are coupled, and/or on the mounting rods. Thus, for example, mounting rod 98*a* may share a common marker with the loading rod that is coupled to tissue anchor 60*a*, indicating that it is desired to mate mounting rod 98*a* with this loading rod.

In some embodiments, loading chamber 86, shown in FIG. 8, facilitates the loading of the implant onto the loading rods, by holding the loading rods within the loading chamber. As further described below, the loading chamber may also crimp the implant, following the loading of the implant onto the loading rods. In some embodiments, as shown in FIG. 8, loading chamber 86 comprises a set of upper latches 90, and a set of lower latches 92, the number of upper latches 90, and the number of lower latches 92, typically matching the number of loading rods 88. Each of upper latches 90 and lower latches 92 is shaped to define a groove 106, which is sized and shaped to fittingly receive one of the loading rods, such that each of the loading rods may be grasped by an upper latch 90 and/or a lower latch 92. The loading chamber may be shaped to define two sections: (i) an upper (proximal) section 21, between the upper and lower latches, and (ii) a lower (distal) crimping section 23. In some embodiments, as shown in FIG. 8, loading rods 88 are fully situated within upper section 21, i.e., loading rods 88 do not extend below the lower latches.

The ensuing description describes the sequence of steps that is performed, in some embodiments, to load an implant onto loading rods 88, and subsequently, to advance the implant along threads 66, with additional reference being made to FIG. 9, which is a schematic illustration of an implant advancer 110, in accordance with some embodiments of the present invention. As further described below, implant advancer 110 is used to advance the implant along threads 66, following the loading of the implant onto the loading rods.

(i) First, as shown in FIG. 8, upper latches 90 of loading chamber 86 are opened, while lower latches 92 grasp the loading rods. Loading shaft 94 is then inserted into upper section 21 of the loading chamber, such that the implant is loaded onto loading rods 88, as described above.

(ii) Following the loading of the implant, the upper latches are closed over base 101 of the loading shaft (thus grasping the loading rods), and the lower latches are then opened. The implant is then pushed by loading shaft 94 along the loading rods and/or threads, into crimping section 23 of the loading chamber. (As the loading shaft is advanced, the loading rods and/or threads pass through the mounting rods and base of the loading shaft, such that the loading shaft moves along the "track" defined by the loading rods and/or threads.)

(iii) Following the pushing of the implant into crimping section 23, the loading shaft is withdrawn into the upper section of the loading chamber. The lower latches are then closed (thus grasping the loading rods), and the upper latches are then opened.

(iv) Loading shaft 94 is removed from the loading chamber, and implant advancer 110 is then inserted into the upper section of the loading chamber. Implant advancer 110 comprises an assembly of flexible pushing rods 78, which are typically equal in number to the number of loading rods. Each pushing rod 78 comprises a hollow pushing-rod tip 80 at the distal end of the pushing rod. Implant advancer 110 is inserted into the loading chamber such that each pushing-rod tip 80 is positioned over a respective loading rod. In other words, the implant advancer is loaded onto the loading rods, by virtue of each loading rod passing through a respective pushing-rod tip of the implant advancer. The pushing-rod assembly is initially supported by an implant-advancer shaft 112 and an implant-advancer disk 108.

(v) The upper latches are then closed over implant-advancer disk 108 (thus grasping the loading rods), and the lower latches are then opened. The implant advancer is then advanced along the loading rods and/or threads, into the crimping section of the loading chamber and up to the implant, such that each pushing-rod tip is in contact with the implant. (As the implant advancer is advanced, the loading rods and/or threads pass through pushing-rod tips 80, such that the implant advancer runs along a "track" defined by the loading rods and/or threads.) Implant-advancer shaft 112 and implant-advancer disk 108 are then withdrawn from the crimping section and into the upper section of the loading chamber.

(vi) The lower latches are closed (thus grasping the loading rods), and the upper latches are then opened. Implant-advancer shaft 112 and implant-advancer disk 108 are then removed from the loading chamber, leaving behind the pushing-rod assembly.

(vii) The implant is then crimped, by virtue of the crimping section of the loading chamber compressing the implant radially inward. As the implant is crimped, the loading rods, and the bottom latches grasping the loading rods, move radially inward. (In some embodiments, the top latches—alternatively or additionally to the bottom latches—grasp the loading rods, and thus move radially inward, during the crimping of the implant.)

(viii) Following the crimping of the implant, the pushing-rod assembly is used to advance the implant over threads 66. (As the implant is advanced, the threads pass through pushing-rod tips 80, such that each pushing rod effectively runs along a "track" defined by the thread over which the pushing rod is advanced.)

Figure 10A:
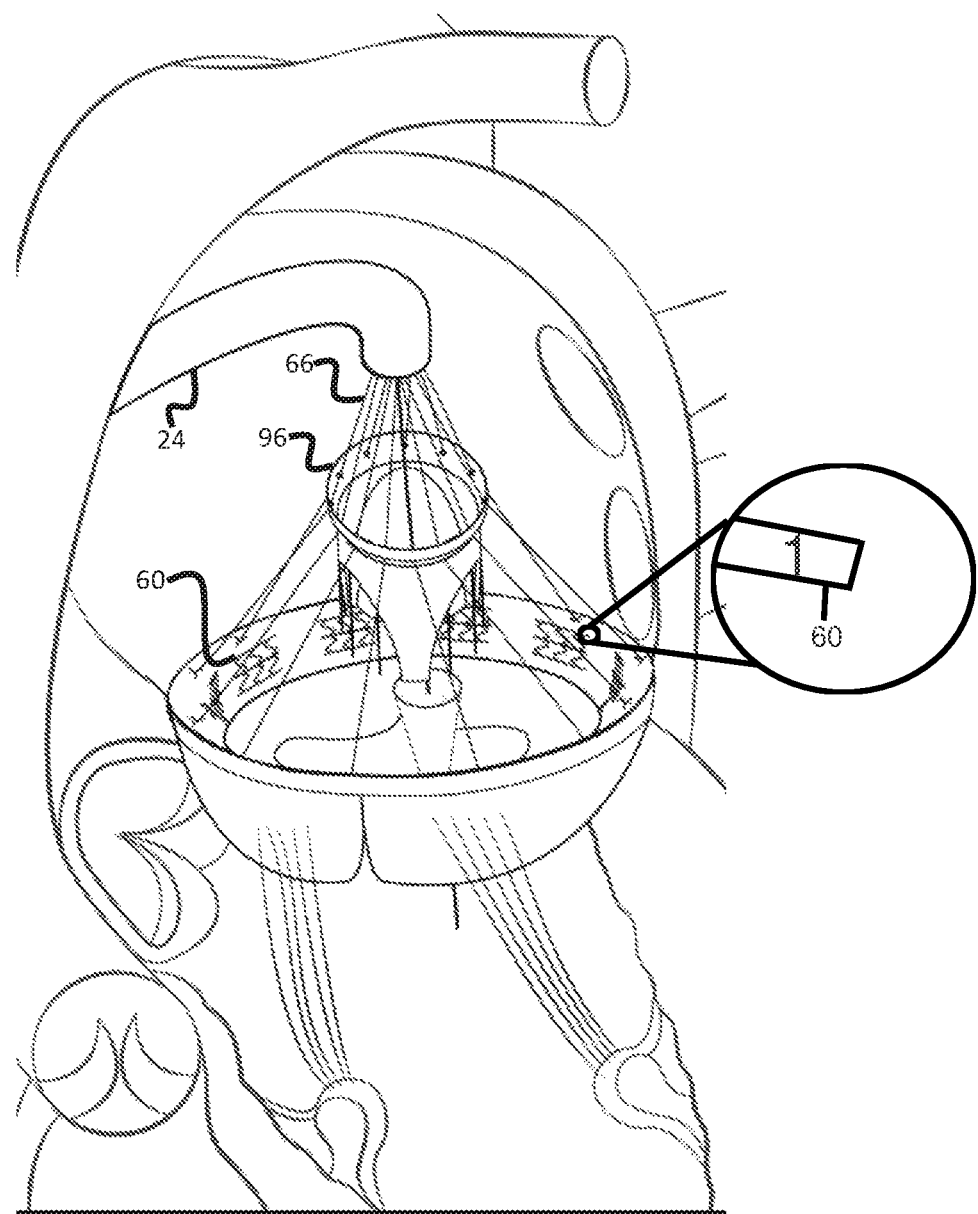
FIGS. 10A-B are schematic illustrations collectively showing an implantation of a replacement valve, in accordance with some embodiments of the present invention.
Figure 10B:
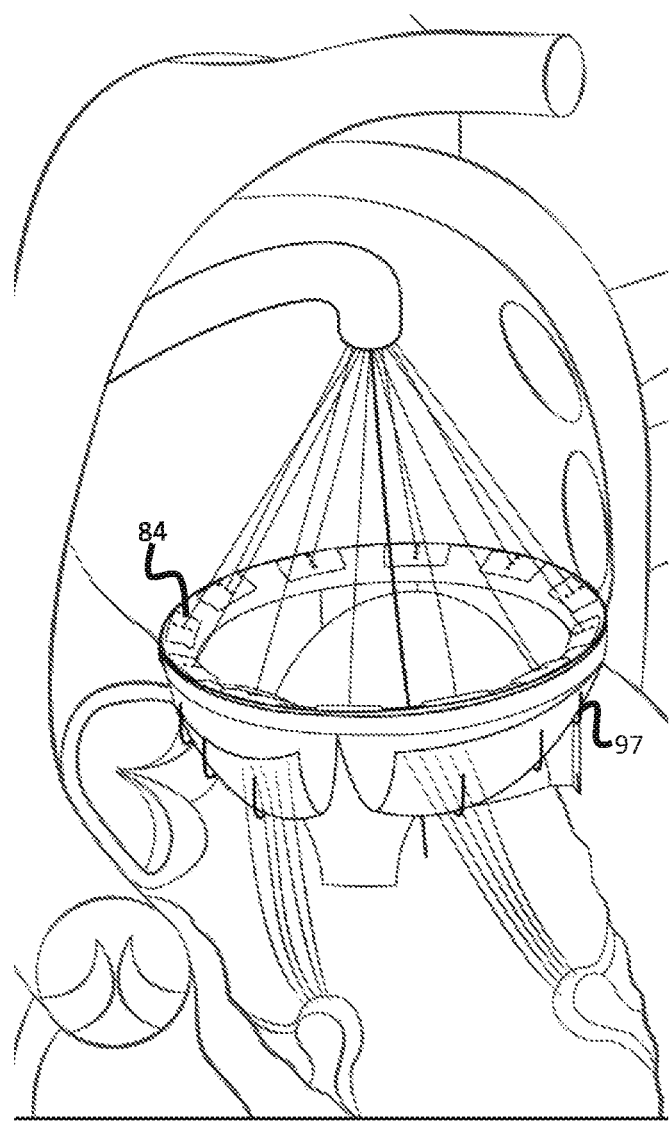
Figure 11A:
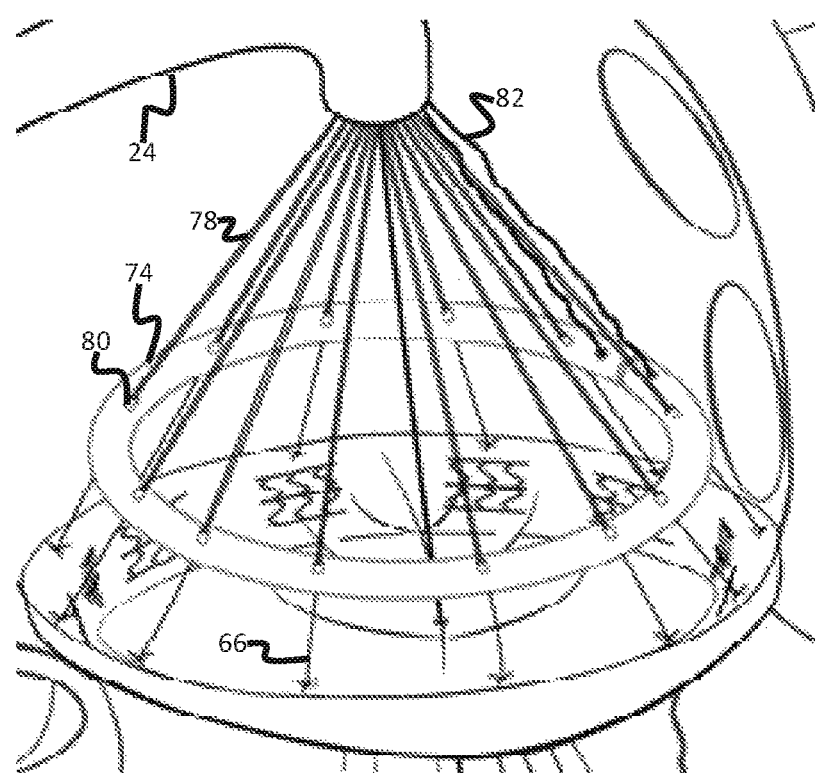
FIGS. 11A-B are schematic illustrations collectively showing an implantation of an annuloplasty ring, in accordance with some embodiments of the present invention.
Figure 11B:
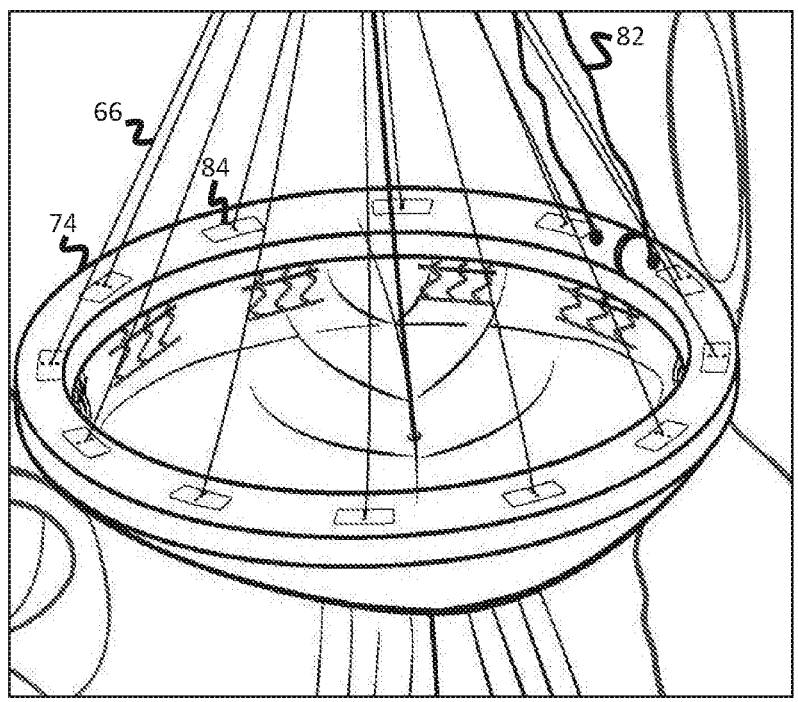

Reference is now made to FIGS. 10A-B, which are schematic illustrations collectively showing an implantation of replacement valve 96, in accordance with some embodiments of the present invention. Reference is also made to FIGS. 11A-B, which are schematic illustrations collectively showing an implantation of an annuloplasty ring 74, in accordance with some embodiments of the present invention. The below description of FIGS. 10A-B and 11A-B generally continues the description of the advancement of the implant that began above with reference to FIGS. 8-9.

FIGS. 10A and 11A show the state of affairs following the advancement of the implant over the majority of the length of the threads. In particular, in these figures, the implant has been advanced, by the assembly of pushing rods 78, through the length of sheath 24, such that the implant is positioned above the mitral valve annulus. (The pushing-rod assembly is not shown in FIG. 10A.) The implant is then pushed into place over the mitral valve annulus, as shown in FIGS. 10B and 11B. Subsequently, pushing rods 78 may be used to advance locking elements 84 (one at a time, or together) over the threads and onto the implant. Alternatively, locking elements 84 may be advanced over the threads together with the annuloplasty ring. As further described below with reference to FIG. 12, locking elements 84 lock the implant in place, i.e., locking elements 84 prevent the implant from migrating from the implantation site. Following the locking of the implant, the threads are pulled taut, and are then cut proximally to the locking elements. The sheath is then withdrawn.

As shown in FIG. 10B, leaflet retainers 97 coupled to replacement valve 96, and/or other leaflet-retaining elements, may be used to hold the natural leaflets of the mitral valve at the perimeter of the mitral valve, such that the natural leaflets do not interfere with the functioning of the replacement valve. The retaining of the natural leaflets of the mitral valve may be performed before or after the locking of the replacement valve.

As shown in FIG. 11B, following the locking of the annuloplasty ring over the mitral valve annulus, an adjustment chord 82, which passes annularly through the annuloplasty ring, may be tightened, thus contracting the mitral valve annulus and bringing the valve leaflets closer together.

Figure 12:
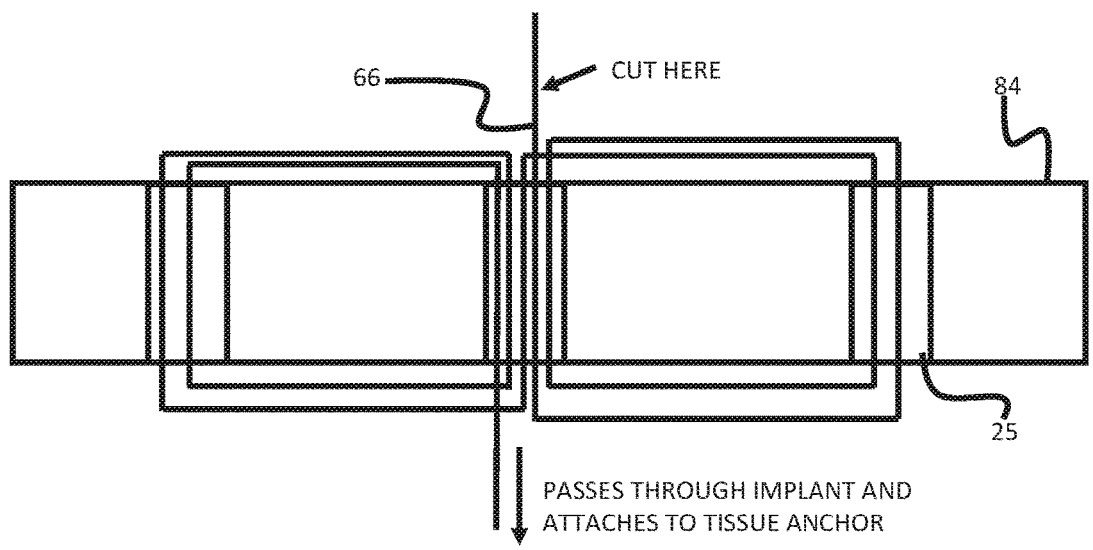
FIG. 12 is a schematic illustration of a locking element, in accordance with some embodiments of the present invention.

Reference is now made to FIG. 12, which is a schematic illustration of a locking element 84, in accordance with some embodiments of the present invention.

Typically, each locking element (comprising, for example, a plate or any other piece of material having a rectangular shape, or any other suitable shape) is shaped to define one or more (e.g., three) apertures 25. (For clarity, the size of apertures 25 is exaggerated in FIG. 12.) Prior to inserting the locking elements into the subject, the proximal end of thread 66 is looped through the apertures, such that the locking element can advance (i.e., move distally) over the thread, but cannot move backward (i.e., proximally) over the thread. The locking element is then advanced over the thread, as described above with reference to FIGS. 10A-B and 11A-B. As further described above, upon the locking element being positioned against the implant, the thread is cut proximally to the locking element. Since the looping of the thread through the locking element does not allow the locking element to move backward over the thread, the implant is effectively locked in place by the locking element.

In general, thread 66 may be looped through apertures 25 in any suitable way, as long as, as described above, the looping allows only forward movement of the locking element. One such suitable way is shown in FIG. 12.

Figure 13A:
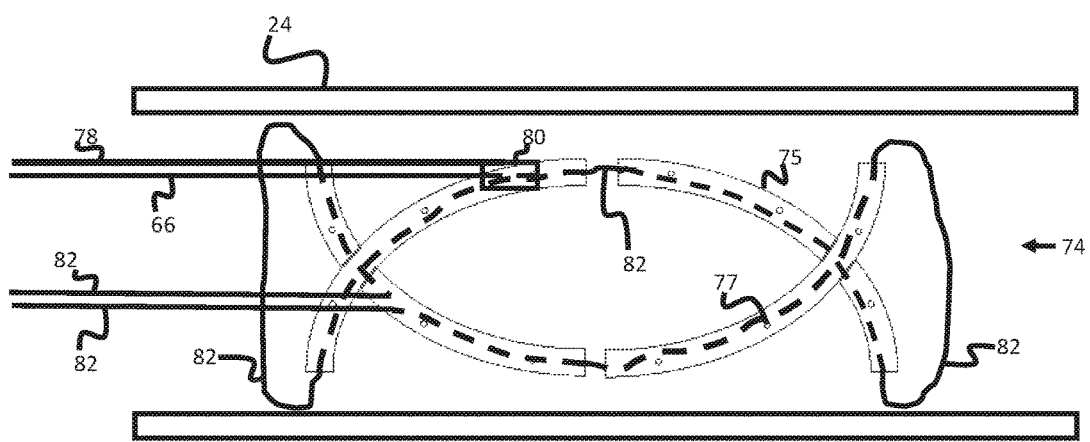
FIG. 13A is a schematic illustration showing the advancement of a disassembled annuloplasty ring through a sheath, in accordance with some embodiments of the present invention.
Figure 13B:
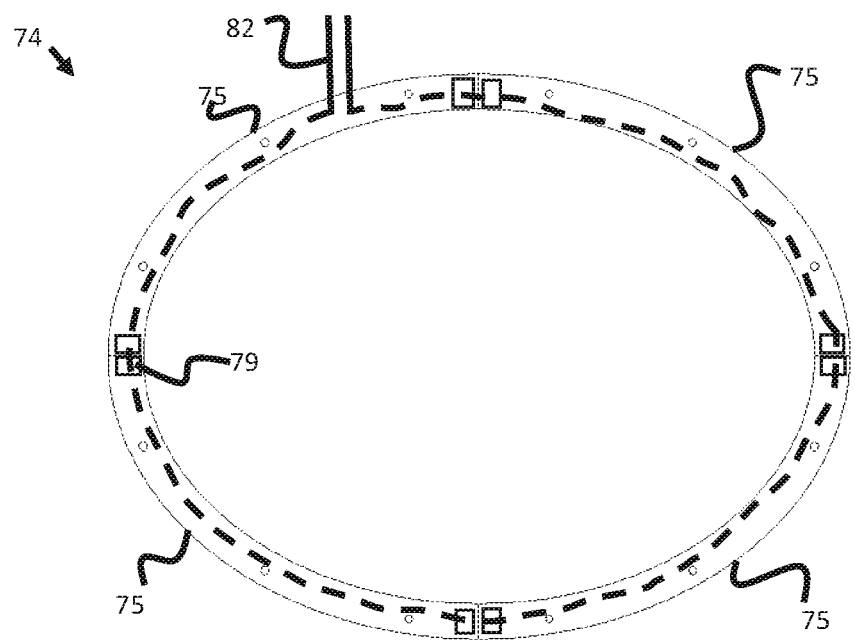
FIG. 13B is a schematic illustration of a reassembled annuloplasty ring, in accordance with some embodiments of the present invention.

Reference is now made to FIG. 13A, which is a schematic illustration showing the advancement of a disassembled annuloplasty ring 74 through sheath 24, in accordance with some embodiments of the present invention, and to FIG. 13B, which is a schematic illustration of a reassembled annuloplasty ring 74, in accordance with some embodiments of the present invention.

In some embodiments, annuloplasty ring 74 comprises a plurality of separable segments 75, such that the annuloplasty ring may be disassembled by separating segments 75 from each other, and then reassembled by reattaching segments 75 to each other. For example, FIG. 13A shows an embodiment in which annuloplasty ring 74 comprises four separable segments 75. To deliver the annuloplasty ring to the implantation site, the annuloplasty ring is first disassembled, and segments 75 are loaded onto the threads. Segments 75 are then advanced through the sheath by pushing rods 78, in the manner shown in, and described above with reference to, earlier figures. That is, each thread 66 passes through a respective implant aperture 77 and a pushing-rod tip 80 positioned over implant aperture 77, such that the implant is pushed, by the pushing rods, over the track defined by the threads.

Upon emerging from the sheath, adjustment chord 82, which passes through all of the segments and thus holds the segments together, is pulled. The tightening of the adjustment chord causes the segments to reattach to each other. In some embodiments, as shown in FIG. 13B, each of the segments comprises a respective coupler, such as a magnet 79, at each of the ends of the segments. As the adjustment chord is pulled and the ends of the segments approach each other, the couplers cause the segments to become reattached to each other (e.g., by virtue of the attraction of magnets 79 to each other), thus further facilitating the reassembly of the annuloplasty ring. Following the reassembly of the annuloplasty ring, the annuloplasty ring is implanted over the valve annulus, and locked in place, as described above with reference to FIG. 11B. The adjustment chord may then be further tightened, such as to constrict the valve annulus.

In some embodiments, alternatively to using the loading and crimping apparatus described above, the implant is preloaded into a guiding catheter (which may be similar to catheter 26), and is then advanced over the threads, while inside the guiding catheter, to the implantation site.

Although the present disclosure relates mainly to a mitral valve, it is noted that—as mentioned above—embodiments described herein may also be applied, mutatis mutandis, to the repair or replacement of a tricuspid valve.

It will be appreciated by persons skilled in the art that the present invention is not limited to what has been particularly shown and described hereinabove. Rather, the scope of embodiments of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. Apparatus, comprising:
an assembly of tubes, each one of the tubes being shaped to define a tube lumen;
a plurality of tissue anchors, each one of the tissue anchors being disposed within a respective one of the tube lumens;
an expandable annular structure, comprising a plurality of teeth, coupled to the assembly of tubes;
a plurality of control wires coupled to the annular structure, configured to position the tubes for deployment of the tissue anchors from the tube lumens at an implantation site, by manipulating the annular structure;
a plurality of loading rods;
a plurality of threads,
a distal end of each of the threads being coupled to a respective one of the tissue anchors, and a proximal end of each of the threads being coupled to a respective one of the loading rods; and
a loading chamber, configured to facilitate delivery of an implant, over the threads, to the implantation site following the deployment of the tissue anchors, by holding the loading rods within the loading chamber while the implant is loaded onto the loading rods.

2. The apparatus according to claim 1, wherein each one of the teeth has a top vertex that is coupled to a respective one of the control wires.

3. The apparatus according to claim 1, wherein the plurality of teeth comprise:
a first annulus of teeth; and
a second annulus of teeth coupled to, and angled radially inward with respect to, the first annulus of teeth.

4. The apparatus according to claim 1, further comprising a plurality of anchor-pushing elements disposed within the tube lumens, each one of the anchor-pushing elements being configured to deploy a respective one of the tissue anchors from a respective one of the tube lumens by pushing the respective one of the tissue anchors.

5. The apparatus according to claim 1, wherein each one of the tubes comprises a pointed distal end.

6. The apparatus according to claim 5, wherein the pointed distal end is curved radially inward.

7. The apparatus according to claim 1, wherein each of the threads passes at least partly through a respective one of the tube lumens.

8. The apparatus according to claim 1,
wherein at least some of the tissue anchors are marked with respective tissue-anchor markers that are different from each other, and
wherein those of the loading rods that are coupled, via the threads, to the marked tissue anchors comprise respective loading-rod markers that correspond to the tissue-anchor markers, respectively.

9. The apparatus according to claim 1, further comprising a loading shaft, configured to load the implant, while the implant is mounted on the loading shaft, onto the loading rods.

10. The apparatus according to claim 1, wherein the loading chamber is further configured to crimp the implant, following the loading of the implant onto the loading rods.

11. The apparatus according to claim 1, further comprising a plurality of locking elements, each locking element of the locking elements being shaped to define one or more apertures, and being configured to lock the implant in place at the implantation site following the delivery of the implant over the threads to the implantation site, by virtue of (i) a respective one of the threads being looped through the apertures such that the locking element cannot move proximally over the respective one of the threads, and (ii) the locking element being positioned against the implant.

12. The apparatus according to claim 1, further comprising the implant, wherein the implant comprises:
an annuloplasty ring comprising a plurality of separable segments shaped to define a plurality of apertures,
the segments being configured to advance to the implantation site, separately from each other, over the threads while the threads pass through the apertures; and
an adjustment chord passing through the ring, the adjustment chord being configured to reassemble the ring at the implantation site upon being tightened.

13. The apparatus according to claim 12, further comprising a plurality of magnets at respective ends of the segments, the magnets being configured to facilitate the reassembly of the ring by virtue of each one of the magnets attracting another one of the magnets.

14. A method, comprising:
deploying, from a catheter, an apparatus that includes:
an assembly of tubes, the tubes being shaped to define respective tube lumens,
a plurality of tissue anchors coupled to respective distal ends of a plurality of threads, each one of the tissue anchors being disposed within a respective one of the tube lumens,
an expandable annular structure that includes a plurality of teeth and is coupled to the assembly of tubes, and
a plurality of control wires coupled to the annular structure;
subsequently to the deploying the apparatus, using the control wires, positioning the tubes at an implantation site by manipulating the annular structure;
subsequently to positioning the tubes, deploying the tissue anchors from the tube lumens at the implantation site;
loading an implant onto a plurality of loading rods that are coupled to respective proximal ends of the threads, while the loading rods are held within a loading chamber; and
subsequently to deploying the tissue anchors and loading the implant, delivering the implant, over the threads, to the implantation site.

15. The method according to claim 14, wherein positioning the tubes comprises adjusting a position of each of the tubes independently from positions of other ones of the tubes.

16. The method according to claim 14, wherein deploying the tissue anchors comprises deploying the tissue anchors by pushing the tissue anchors from within the tube lumens.

17. The method according to claim 14, further comprising, prior to deploying the tissue anchors, passing respective distal ends of the tubes through tissue.

18. The method according to claim 17, wherein passing the respective distal ends of the tubes through the tissue comprises passing the respective distal ends of the tubes through tissue of an annulus of a valve of a heart such that the tubes emerges from the tissue at an anchoring site on a radially-inward-facing face of the annulus, and wherein deploying the tissue anchors comprises deploying the tissue anchors at the anchoring site.

19. The method according to claim 18, wherein the anchoring site is within an atrium of the heart.

20. The method according to claim 18, wherein the anchoring site is within a ventricle of the heart.

21. The method according to claim 14, further comprising, using a plurality of locking elements, locking the implant in place at the implantation site, by:
looping a respective one of the threads through one or more apertures of each locking element of the locking elements, such that the locking element cannot move proximally over the respective one of the threads, and
subsequently, advancing the locking elements over the threads such that the locking elements are positioned against the implant at the implantation site.

22. The method according to claim 14, wherein the implant includes an annuloplasty ring including a plurality of separable segments shaped to define a plurality of apertures, and wherein delivering the implant comprises:
passing the threads through the apertures; and
subsequently, advancing the segments of the ring, separately from each other, over the threads.

23. The method according to claim 22, further comprising, subsequently to advancing the segments of the ring over the threads, reassembling the ring by tightening an adjustment chord that passes through the ring.

24. The method according to claim 14,
wherein at least some of the tissue anchors comprise respective tissue-anchor markers that are different from each other,
wherein at least some of the loading rods comprise respective loading-rod markers that are different from each other, and
wherein the method further comprises, prior to loading the implant onto the loading rods:
acquiring at least one image of the tissue-anchor markers, and
responsively to the image and to the loading-rod markers, aligning the implant with respect to the loading rods.

25. The method according to claim 14, wherein loading the implant onto the loading rods comprises:
mounting the implant onto a loading shaft, and
using the loading shaft, loading the implant onto the loading rods.

* * * * *